(12) United States Patent
Albohr et al.

(10) Patent No.: US 8,154,283 B2
(45) Date of Patent: Apr. 10, 2012

(54) METHOD AND APPARATUS FOR AUTOMATICALLY ANALYZING THE CHARACTERISTICS OF AN ELASTOMERIC MATERIAL INCLUDED IN A TIRE

(75) Inventors: Oliver Albohr, Höchst (DE); Luciano Garro, Orango (IT); Udo Kuhlmann, Aschaffenburg (DE)

(73) Assignee: Pirelli Tyre S.p.A., Milan (IT)

( * ) Notice: Subject to any disclaimer, the term of this patent is extended or adjusted under 35 U.S.C. 154(b) by 137 days.

(21) Appl. No.: 12/086,863

(22) PCT Filed: Nov. 17, 2006

(86) PCT No.: PCT/EP2006/068635
§ 371 (c)(1),
(2), (4) Date: Dec. 3, 2008

(87) PCT Pub. No.: WO2007/071511
PCT Pub. Date: Jun. 28, 2007

(65) Prior Publication Data
US 2009/0179640 A1 Jul. 16, 2009

(30) Foreign Application Priority Data
Dec. 22, 2005 (EP) .................................. 05112834

(51) Int. Cl.
*G01V 3/00* (2006.01)
(52) U.S. Cl. ..................... 324/307; 324/309; 324/318
(58) Field of Classification Search .......... 324/300–322; 73/146; 156/367, 460, 351; 526/79; 600/459, 600/407–435
See application file for complete search history.

(56) References Cited

U.S. PATENT DOCUMENTS

| | | | | |
|---|---|---|---|---|
| 1,763,297 A | * | 6/1930 | Fowler | 156/460 |
| 3,281,304 A | * | 10/1966 | Black et al. | 156/351 |
| 3,318,745 A | * | 5/1967 | Black et al. | 156/111 |
| 3,323,970 A | * | 6/1967 | Black et al. | 156/396 |

(Continued)

FOREIGN PATENT DOCUMENTS
WO WO 2007071511 A1 * 6/2007

OTHER PUBLICATIONS

Watanabe; "Nuclear Magnetic Resonance Imaging," Nuclear Magnetic Resonance, vol. 30, pp. 453-476, (2001).

(Continued)

*Primary Examiner* — Melissa Koval
*Assistant Examiner* — Tiffany Fetzner
(74) *Attorney, Agent, or Firm* — Finnegan, Henderson, Farabow, Garrett & Dunner, LLP

(57) ABSTRACT

A method and an apparatus for analyzing at least one material characteristic of a tire wherein nuclear magnetic resonance measuring is applied to a tread block of the tire by means of a nuclear magnetic resonance measuring system including a nuclear magnetic resonance sensor. The apparatus includes a magazine for storing at least one tire, a nuclear magnetic resonance measuring system including a nuclear magnetic resonance sensor, positioning means for moving the nuclear magnetic resonance sensor in at least one direction with respect to the tire, a driving means for driving the tire with respect to its rotational axis, a control unit for controlling the positioning means and the driving means, and a computer connected with the control unit and the nuclear magnetic resonance measuring system. It is possible to automatically analyze the material characteristics of a plurality of tires within a short time.

18 Claims, 5 Drawing Sheets

U.S. PATENT DOCUMENTS

| | | | | |
|---|---|---|---|---|
| 3,524,784 A | * | 8/1970 | Isaksson et al. | 156/367 |
| 3,772,256 A | * | 11/1973 | Delaney et al. | 526/79 |
| 4,989,449 A | * | 2/1991 | Monch | 73/146 |
| 5,153,899 A | | 10/1992 | Curry | |
| 5,853,005 A | * | 12/1998 | Scanlon | 600/459 |
| 6,269,689 B1 | | 8/2001 | Alexander | |
| 6,856,132 B2 | * | 2/2005 | Appel et al. | 324/303 |
| 6,946,838 B2 | * | 9/2005 | Corver et al. | 324/307 |
| 2002/0084783 A1 | | 7/2002 | Blumich et al. | |
| 2004/0090230 A1 | * | 5/2004 | Appel et al. | 324/307 |
| 2004/0251904 A1 | * | 12/2004 | Corver et al. | 324/321 |
| 2009/0179640 A1 | * | 7/2009 | Albohr et al. | 324/309 |

OTHER PUBLICATIONS

Blümich et al., "NMR Imaging of Materials," Clarendon Press—Oxford, pp. 415-423, 439-444, and 509-525, XP002379411, (2000).

Shimizu, M. et al., "Radiation Type Tire Inspecting Apparatus," Patent Abstracts of Japan of JP. Publication No. 52-079988, published on Jul. 5, 1977, 1 Sheet.

G. Guthausen, et al.; Quality Control with NMR: Selected Examples and Application in Polymer Industry; KGK Kautschuk Gummi Kunstoffe, $56^{th}$ Edition Jahrgang, Nr. Nov. 2003 (4 pages).

N. Goga, et al.; Noninvasive quality control in the tire production with NMR-Mouse®; Newsletter; Zentrum für Magnetische Resonanz e.V.; Mar. 2006; vol. 11; Rott, Germany (2 pages), Color Reference.

* cited by examiner

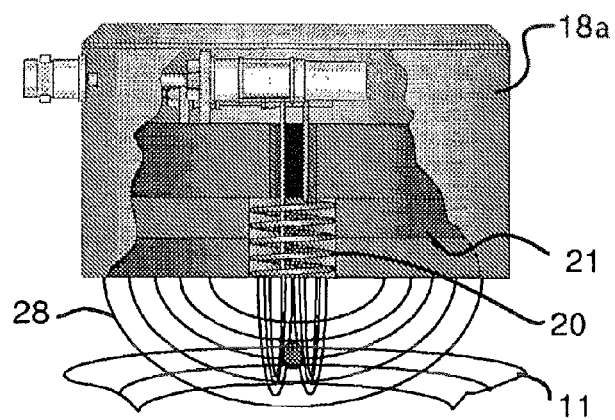
Fig. 5
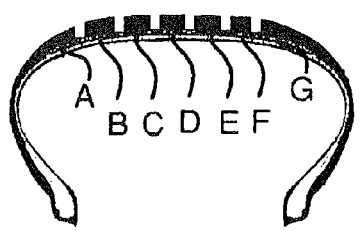
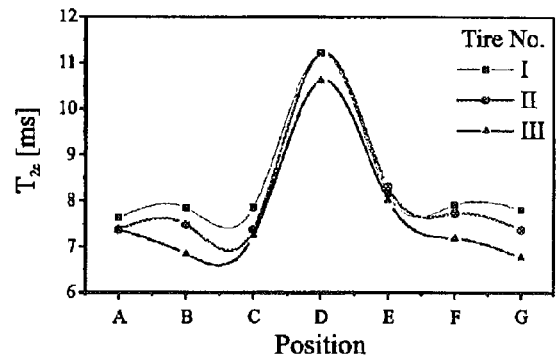
Fig. 6a  Fig. 6b

METHOD AND APPARATUS FOR AUTOMATICALLY ANALYZING THE CHARACTERISTICS OF AN ELASTOMERIC MATERIAL INCLUDED IN A TIRE

CROSS REFERENCE TO RELATED APPLICATIONS

This application is a national phase application based on PCT/EP2006/068635, filed Nov. 17, 2006, and claims the priority of European patent application no. 05112834.6, filed Dec. 22, 2005, the content of both of which is incorporated herein by reference.

BACKGROUND OF THE INVENTION

1. Field of the Invention

The present invention relates to a method for analyzing at least one characteristic of an elastomeric material included in a tire, wherein a NMR measuring is applied to a tread block of the tire by means of a NMR measuring system including a NMR sensor.

Moreover, the present invention also relates to an apparatus for carrying out the method mentioned above.

2. Description of the Related Art

Accordingly the present invention makes use of an analyser based on NMR (Nuclear Magnetic Resonance) measurements.

Quality control at the end of the manufacturing process is of great importance in the rubber industry, in particular in the manufacturing of tires.

Apart from non-destructive methods for quality check of tires uniformity and integrity, most of the methods commonly used for quality control of elastomeric material included in tires, are destructive and require test samples to be taken out from the tire.

Efforts in order to find non-destructive methods have been already made in the art.

For example, NMR (Nuclear Magnetic Resonance) measurements are known in the material research in order to analyze the material characteristics. To this aim, by means of a NMR measuring system a NMR signal is generated in an area adjacent the NMR sensor surface, which signal is measured in order to characterize the properties of the materials in the vicinity of the surface adjacent to the NMR sensor. NMR measuring systems of this kind are commercially distributed, for example, by BRUKER GmbH, 76287 Rheinstetten, Germany.

The material to be examined is magnetized so the spin of the atoms will be adjusted according to the magnetic field lines. The adjustment of the spin of atoms is disturbed by an additionally applied electromagnetic signal (disturbing signal). After switching off the additional electromagnetic field, the spin of the atoms will go back to their alignment of the magnetic field lines. At the moment of going back to their originally orientation they will send out a feedback signal which is characteristic for the environment or for the material characteristics. Usually, the disturbing signal is formed by a plurality of pulse signals.

A general description relative to NMR measuring method may be found, for example, in "Nuclear Magnetic Resonance" (2001), Vol. 30, pg. 453-476.

United States Patent Application US 2002/0084783 discloses an apparatus for examining flat goods of polymeric material having reinforcement structures embedded therein, said apparatus being provided with a number of NMR sensor probes on a measuring surface of an examination body for nuclear magnetic resonance imaging analysis of the flat goods.

A "Newsletter" issued on 1 Mar., 2005 by "Zentrum Für Magnetische Resonanz E. V." discloses the use of NMR sensors to control the quality, by non-destructive measurements, not only of test samples, but also of production intermediates and final products, in rubber industry, in particular in tire production.

For providing such NMR measurements in the tire field, the positioning of the NMR sensor must be as accurate as possible. Therefore, usually, the NMR measurements are manually performed so as to obtain repeatable and reliable measurements.

However, said manually performing measurements besides being time consuming, do not allow to analyze a high number of samples (i.e. tires) and, consequently, are not advantageously applicable on an industrial scale.

SUMMARY OF THE INVENTION

The Applicant has faced the problem of providing a method for analyzing the characteristics of an elastomeric material included in a tire able to be advantageously employed on an industrial scale and to give repeatable and reliable results in short times. Therefore, the method should be performed automatically.

The Applicant has now found that it is possible to automatically perform the above reported method by using a NMR sensor. In particular, the Applicant has found a method which provides both an accurate positioning of the NMR sensor with respect to the tire surface to be analyzed and the characteristics of an elastomeric material included in said tire, in an automated way.

As known, a tire comprises a tread band including plurality of tread blocks and profile grooves positioned between the tread blocks, said profile grooves and said tread blocks forming the contact surface of a tire which is contacting the road during driving.

Applicant has noticed that, in case the tread band of a tire has to be analyzed, in order to perform said method, it is very important to position the NMR sensor in correspondence of a tread block and not even partially on a profile groove. Therefore, an accurate positioning of the NMR sensor is required for achieving repeatable and reliable quality results for a plurality of tires within short times.

According to a first aspect, the present invention relates to a method for analyzing at least one characteristic of an elastomeric material included in a tire, wherein a NMR measuring is applied to a tread block of the tire by means of a NMR measuring system including a NMR sensor, said method being characterised in that:

a) said tread block of the tire is automatically detected by means of a first NMR measuring cycle including the following steps:
   aa) positioning said NMR sensor adjacent to the external surface of the tire;
   ab) applying a first exciting signal to a portion of said tire including an elastomeric material by said NMR sensor;
   ac) receiving a first feedback signal from said elastomeric material excited by said first exciting signal;
   ad) storing the first feedback signal and the position of the NMR sensor;
   ae) repeating steps aa) to ad) at different positions of the tire;
   af) detecting tread block by analyzing the intensities of feedback signals;

b) carrying out a second NMR measuring cycle at said tread block including the following steps:
ba) applying a second exciting signal to said tread block including an elastomeric material by said NMR sensor;
bb) receiving a second feedback signal from said elastomeric material excited by said second exciting signal;
bc) comparing second feedback signals with reference signals to determine at least one-characteristic of the elastomeric material.

According to the invention a NMR measuring system is used both for detecting a tread block of the tire and for analyzing at least one characteristic of the elastomeric material of the tread block detected. The tread block is automatically detected by a first NMR measuring cycle carried out at different positions of the tire. Since a tread block is limited by profile grooves and the feedback signals of a tread block and a profile groove are different the tread block can be detected by means of the first NMR measuring cycle. In the second NMR measuring cycle the reference signals are obtained from reference tires analyzed by the method mentioned above.

According to one preferred embodiment, in said first NMR measuring cycle said first exciting signal is formed by a single pulse or a small amount of pulses. Such signals having only small energy are sufficient to detect the existence of a tread block or a profile groove. On the other hand, in said second NMR measuring cycle the second exciting signal is advantageously formed by a plurality of pulses. Such a signal is necessary to determine the characteristics of the elastomeric material.

According to one preferred embodiment, it is advantageously that said NMR sensor is moved in at least one direction (x, y, z) with respect to the surface of the tire. Thus, the NMR measuring can be carried out at a plurality of measuring positions.

It is advantageous, that in conducting the first NMR measuring cycle the NMR sensor is arranged with small distance from the surface of the tire. In practice, a distance of from 1 to 3 mm is appropriate. Such a distance allows free rolling of the tire during the tread block finding measurements.

In contrast, in conducting the second NMR measuring cycle the NMR sensor is advantageously arranged on the surface of the tire. Preferably, the NMR sensor is directly in contact with the surface of the tire.

According to one preferred embodiment, after conducting said second NMR measuring cycle the NMR sensor is moved from the surface of the tire to rotate the tire to the next measuring point.

According to one preferred embodiment, after having measured a predetermined number of measuring points of the tire the NMR sensor can be moved in horizontal direction (x) to a plurality of tires held in a magazine. Therefore, a plurality of tires can be analyzed automatically and in short times.

According to a further aspect, the present invention also relates to an apparatus for carrying out the method according to invention, comprising:
 a magazine for taking up and positioning at least one tire;
 a NMR measuring system including a NMR sensor;
 a positioning means for moving said NMR sensor in at least one direction with respect to the tire;
 a driving means for driving the tire with respect to its rotational axis;
 a control unit for controlling the positioning means and driving means;
 a computer connected with the control unit and the NMR measuring system.

According to one preferred embodiment, said computer includes storing means for storing NMR measuring programme and/or NMR sensor control programme.

According to one preferred embodiment, said NMR measuring system automatically detects a tread block of the tire by generating a first exciting signal formed as one pulse or a small amount of pulses and receiving a first feedback signal. On the other hand, the NMR measuring system advantageously analyses the characteristics of the elastomeric material by generating a second exciting signal including a plurality of pulses and receiving a second feedback signal.

According to one preferred embodiment, said positioning means for moving the NMR sensor comprise a driven carriage guided in horizontal direction (x) on a rail. The carriage is controlled by said control unit.

According to a further preferred embodiment, the positioning means for moving the NMR sensor comprise a vertical actuator for positioning the NMR sensor in vertical direction (z) and/or a transverse actuator for adjusting the position of the NMR sensor in transverse direction.

According to one preferred embodiment, said magazine is adapted to hold a plurality of tires. Thus, a plurality of tires can be automatically analyzed on an industrial scale.

According to one preferred embodiment, said apparatus includes a camera or another sensor for monitoring the position of the NMR sensor.

According to one preferred embodiment, said driving means comprise at least one driven transport roll cooperating with the surface of the tire. Thus, the tire can be turned around its rotational axis.

It is further advantageous, that lateral rolls for fixing the tire and/or a pivoted retainer are provided.

It is further advantageous, that said control means is adapted for driving the driving means to predetermined measuring points.

By means of the method and the apparatus according to the present invention it is possible to automatically analyze the characteristic of the elastomeric material included in a tire at different positions at the surface of the tire. Further, it is possible to repeat the measuring method accurately for each tire and to obtain reliable results. In particular, a tire can be "scanned" by a plurality of NMR measurements. Furthermore, it is possible to check in a non-destructive manner a plurality of tires within short times.

As reported above, the apparatus for carrying out the method according to the present invention is capable to checking different sizes of tires. So it is possible to check a tire having a width of e.g. 195 mm, wherein the next tire is 225 mm and so on.

BRIEF DESCRIPTION OF THE DRAWINGS

An analyzing apparatus embodying the invention will now be described, by way of examples only, with reference to the accompanying schematic drawings in which:
FIG. 5 shows schematic illustration of a NMR sensor on a tire;
FIG. 6a shows a section of a tire showing a plurality of tread blocks and profile grooves;

FIG. 6b shows a graphical illustration of measuring results at different positions of three different tires.

DETAILED DESCRIPTION OF THE INVENTION

Figure 1:
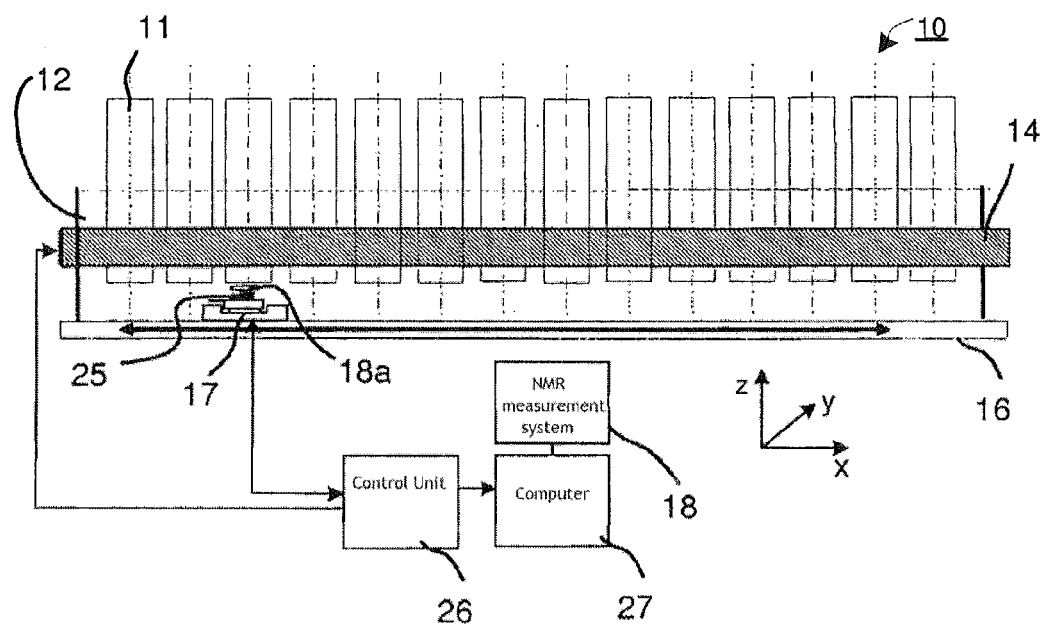
FIG. 1 shows a schematic illustration of an analyzing apparatus comprising a magazine for a plurality of tires.

Referring to FIG. 1 a schematic illustration of an apparatus 10 for analyzing the characteristics of an elastomeric material included in a tire 11 is shown. The apparatus 10 comprises a magazine 12 for storing a plurality of tires 11. The tires 11 are vertically arranged in the magazine 12 with distance from each other.

Within the magazine 12 a rail 16 is arranged extending in a horizontal direction x. A driven carriage 17 is movable guided in horizontal direction x on the rail 16. The carriage 17 is provided for carrying a NMR sensor 18a of a NMR measuring system 18. This NMR measuring system 18 includes besides the NMR sensor 18a an electronic unit (not shown). The NMR measuring system 18 is distributed, for example, by BRUKER GmbH, 76287 Rheinstetten, Germany.

For positioning the NMR sensor 18a in vertical direction z a vertical actuator 25 is mounted on the carriage 17. Thus the NMR sensor 18a can be positioned at a predetermined distance to the tire 11. The NMR sensor 18a is coupled with a control unit 26, wherein the control unit 26 is connected to a computer 27.

The plurality of tires 11a is placed on transport rolls 14 cooperating with the surface of the tire 11. The transport rolls 14 are drivable on a command sent out by the control unit 26. By driving the transport rolls 14 the tire 11 to be tested is rotated to position the NMR sensor 18a in different measuring points ($P_n$) (not represented in FIG. 1) of the tire 11.

Figure 2:
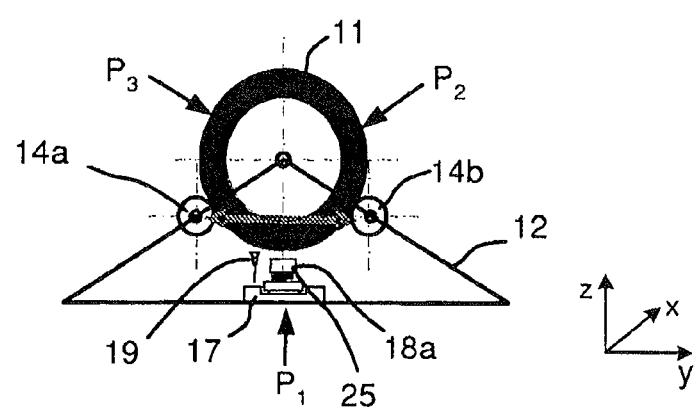
FIG. 2 shows a side view of the analyzing apparatus.

According to FIG. 2 at least two transport rolls 14a and 14b are provided within the magazine 12. By adjusting the distance between the transport rolls 14a and 14b the diameter of the tire 11 can be changed. Thus, the magazine 12 is capable of accommodating tires 11 having different sizes or diameters. The position of the transport rolls 14a and 14b is movable in the y direction. Further, the different measuring points $P_1$, $P_2$ and $P_3$ are illustrated.

For supporting the positioning of the NMR sensor 18a under the tire 11a camera 19 or another sensor maybe placed on the carriage 17 for displaying the different measuring points ($P_n$) on a display device (not represented in FIG. 2).

Figure 3:
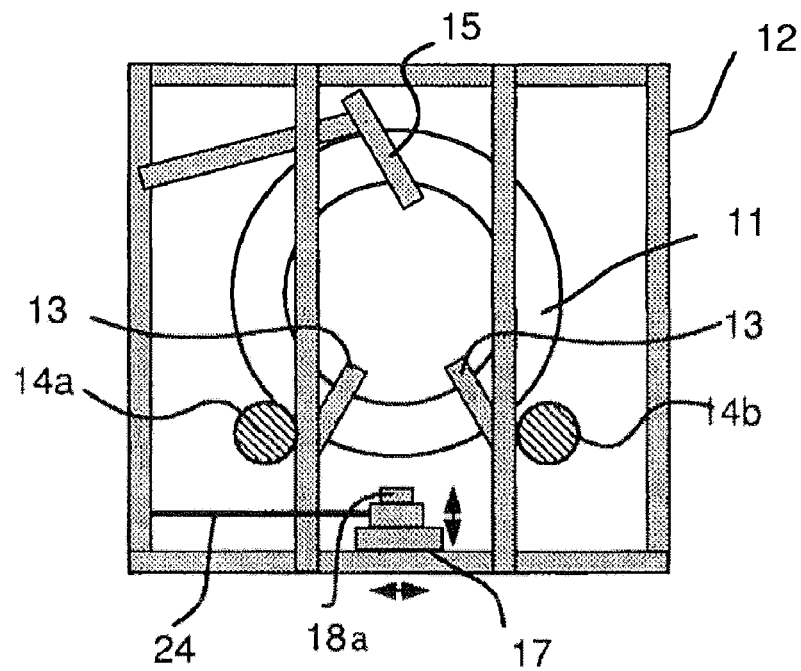
FIG. 3 shows a side view of a modified configuration with an alteration magazine
Figure 4:
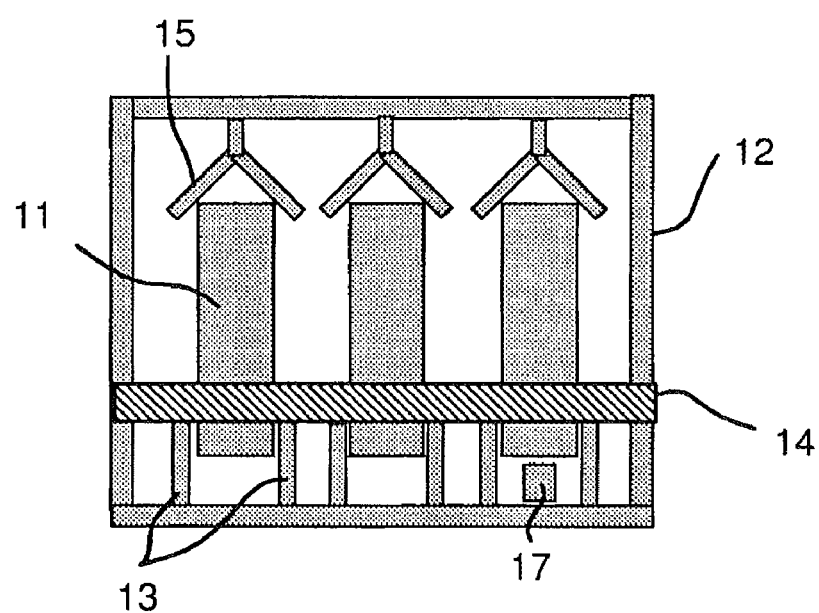
FIG. 4 shows a schematic illustration of a front view of a magazine according to the illustration of FIG. 3.

In the following, an alternative magazine is described with reference to the FIGS. 3 and 4. The magazine 12 includes three tires 11. The tires 11 are fixed by lateral rolls 13 which are located on the right and left side of each tire 11. Further, there are transport rolls 14 on which the tires 11 are placed. The transport rolls 14 are provided for driving the tires 11 after the measuring procedure has taken place. To fix the tires 11 in its vertical position pivoted retainers 15 are provided which are keeping the tires 11 in contact with the transport rolls 14. As further shown in FIG. 3, the carriage 17 provided with the NMR sensor 18a is capable of being moved in y direction by moving a traverse actuator 24. Further, by moving the vertical actuator 25, which is not illustrated in FIGS. 3 and 4 the NMR sensor 18a maybe positioned in contact with the external surface of the tire 11.

FIG. 5 shows a NMR sensor 18a as used in the apparatus 10. The NMR sensor 18a includes a permanent magnet 21 and a coil 20. The permanent magnet 21 applies a magnet field to a portion of a tire 11 including an elastomeric material. The magnet field caused by the permanent magnet 21, is illustrated by the magnetic field lines 28. The coil 20 is used as an exciting coil in the exciting mode and as a receiving coil in the receiving mode. The field lines of coil 20 caused by the first exciting signal are applied to a portion of a tire 11 including an elastomeric material. Since the spins of atoms of said elastomeric material are aligned in the direction of the magnetic field lines 28 due to the permanent magnetic field caused by the permanent magnet 21 the spins of atoms of said elastomeric material are disturbed in their alignment by said first exciting signal sent out by the coil 20. After applying a first exciting signal and/or a second exciting signal to a portion of a tire 11 including an elastomeric material, the coil 20 is switched to the receiving mode. After switching off the exciting signal the spins of atoms of said elastomeric material will go back to their original alignment due to the permanent magnetic field 28. During going back to their original alignment the atoms send out a second feedback signal which is received by the coil 20. This second feedback signal is indicative for at least one characteristic of said elastomeric material included in the tire.

The difference of the material characteristics is illustrated in respect to the FIGS. 6a and 6b. It is illustrated that a tire may be measured on different locations A-G. FIG. 6b shows the respective measuring results in a diagram. In the x axis the different measuring positions have been reported; in the y axis the relaxation times ($T_{2c}$) have been reported. Three different tires I, II, III were measured. As can be seen in the diagram the received second feedback signal at the position D is the strongest one for all tires I-III. So, if there is a material defect at one of the positions A-G the curves I, II, III will differ at the respective location from the reference value or from the reference tire. In the FIG. 6b no deviations are indicated in the three different tires I, II, III.

Figure 7:
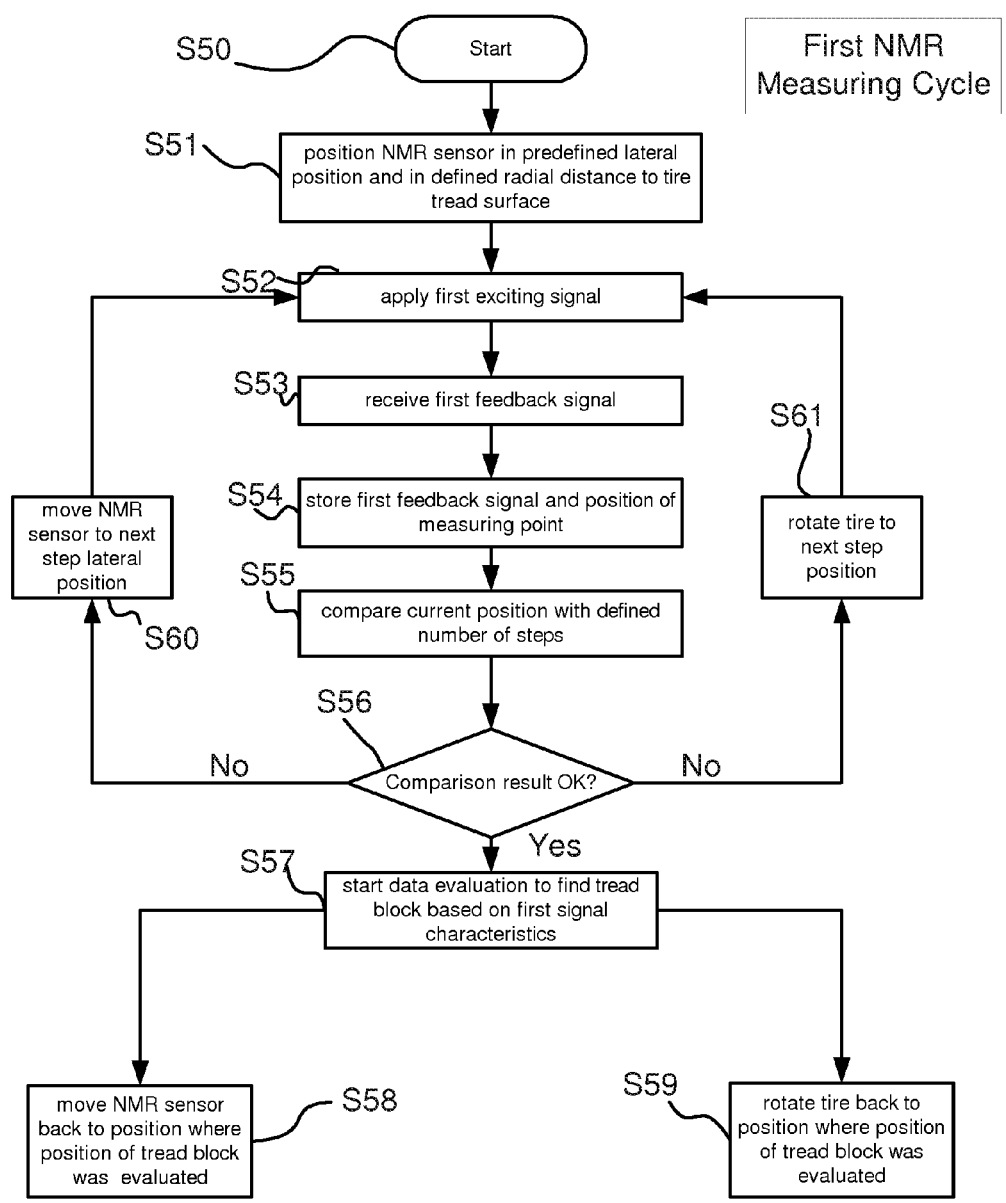
FIG. 7 shows a flowchart illustrating the first NMR measuring cycle according to the present invention.
Figure 8:
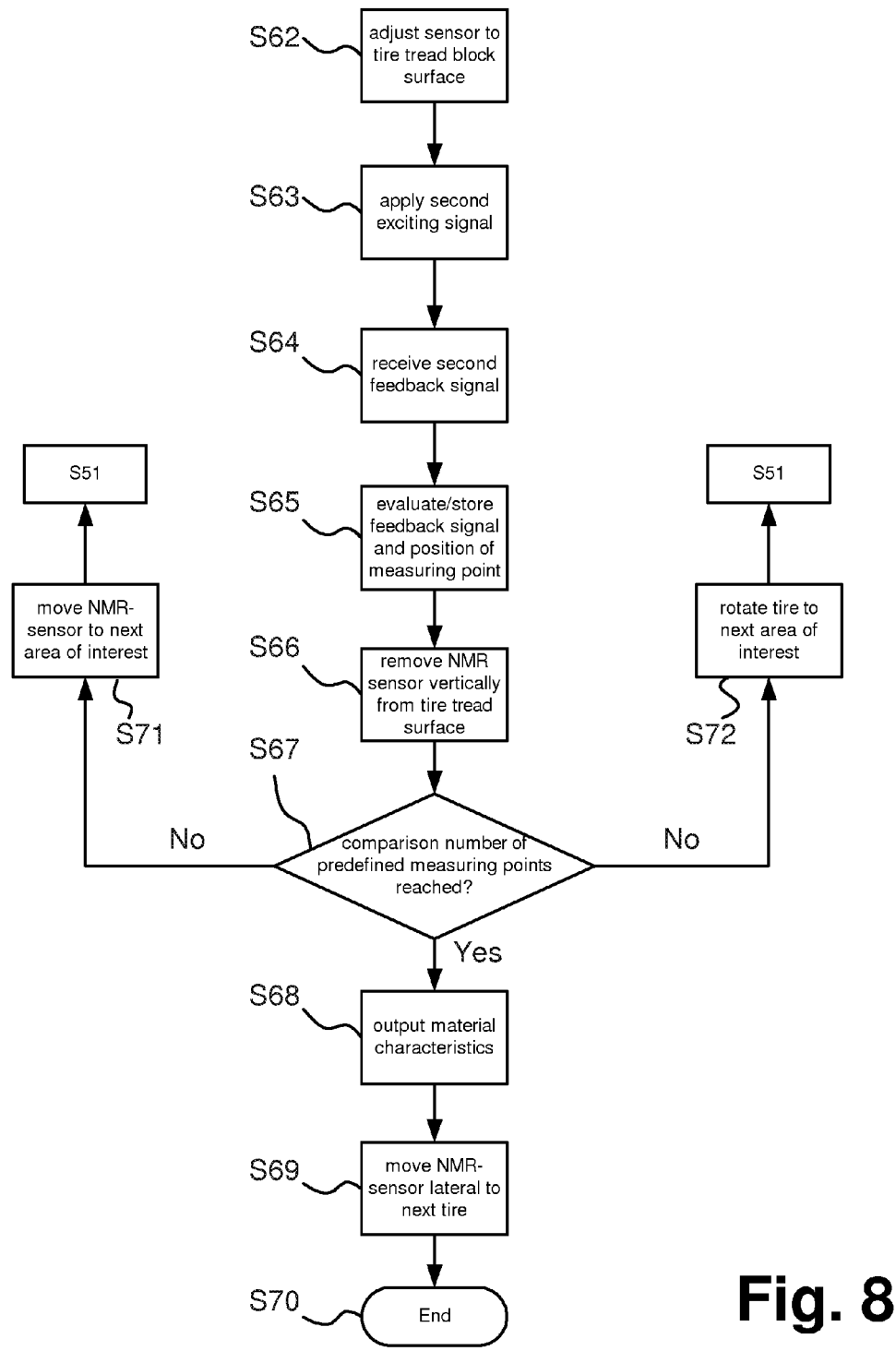
FIG. 8 shows a flowchart illustrating the second NMR measuring cycle according to the present invention.

In the following the procedure of analyzing of material characteristics according to the invention will be explained referring to FIGS. 7 and 8 illustrating flow charts.

The flowchart according to FIG. 7 concerns the first NMR measuring cycle in which a tread block of the tire 11 is automatically detected.

Before starting the first measuring cycle a plurality of tires 11 is arranged in the magazine 12. By driving the transport rolls 14, positioning the lateral rolls 13 and the pivoted retainers 15 the tires 11 are adjusted in their position within the magazine 12.

In step S50 the first NMR measuring cycle is started in order to automatically detect a tread block of the tire 11. According to step S51 the NMR sensor 18a is positioned under the external surface (i.e. the external surface of a tire tread band) of the first tire (11) to be analyzed, the NMR sensor 18a is vertically lifted until the NMR sensor 18a is positioned to a predefined radial distance of about 1 to 3 mm from the external surface of the tire 11 to be tested. In addition the NMR sensor is arranged in predefined lateral position with respect to the tire 11.

In step S52, a first exciting signal is applied by the NMR sensor 18a to a portion of the tire 11. The first exciting signal is formed by a single pulse or a so-called Hahn echo which excites the atoms within the portion of the tire 11. After having applied the first exciting signal the NMR sensor 18a is switched to the receiving mode in order to receive a first feedback signal (step S53). During going back to their original alignment the atoms send out a first feedback signal which is received by the NMR sensor 18a. This first feedback signal is stored together with the position of the measuring point in the computer 27 (step S54).

In step S55 the current position is compared with a defined number of steps. If the comparison result in step S56 is "No", the NMR sensor 18a (step S60) will be moved to next step lateral position and/or the tire 11 (step S61) will be rotated to next step position. Then, step S52 and the following steps are carried out again.

If the comparison result is "Yes", the computer 27 will start data evaluation to find a tread block based on first feedback signal characteristics (step S57). After determination of a tread block the NMR sensor 18a is moved to the position where the tread block was evaluated (step S58). In addition, the tire 11 will be rotated back to the position where position of tread block was evaluated (step S59). At this point the first NMR measuring cycle is finished.

The following second NMR measuring cycle is explained referring to FIG. 8 illustrating a flow chart.

At the beginning, the NMR sensor 18a is moved according to step S62 in a direction substantially perpendicular to the tire 11 in order to directly contact the external surface of the detected tread block of tire 11. The procedure proceeds with step S63, wherein the second exciting signal is supplied to the tire 11 by the NMR sensor 18a which is in the exciting mode. The second exciting signal is normally formed by a plurality of pulses which are sent out by the coil 20 of the NMR sensor 18a. This second exciting signal is called CPMG echo also. After having excited the atoms within the elastomeric material included in the tire 11, the NMR sensor 18a is switched again to the receiving mode. At the moment of going back to their original alignment the atoms send out a second feedback signal which is received by the NMR sensor 18a (step S64). In step S65, these second feedback signal is evaluated by the NMR measuring system 18 and stored together with the position of the measuring point in the computer 27.

The next step S66, includes a movement of the NMR sensor 18a from the tire surface. Then, in step S67, it is determined whether a predetermined number of measuring points ($P_n$) is reached. In case of a non-completed test which means that the comparison results in "No", the NMR sensor 18a is moved (step S71) and/or the tire 11 is rotated (step S72) to the next area of interest. Then, the first NMR measuring cycle starting in step S51 is carried out in order to determine a further tread block.

If in step S67 the comparison results in "Yes", the characteristics of the elastomeric material are outputted by the computer 26 (step S68).

Then, in step S69, the NMR sensor 18a is horizontal moved by the driven carrier 17 on the rail 16 to the next tire 11 adjacent to the tire 11 already tested so ending the method according to the present invention in step S70. Subsequently, the first and second NMR measuring cycle is carried out again to analyze the next tire.

By means of the method and the apparatus according to the present invention, it is possible to automatically analyze the material characteristics of at least one tire, preferably of a plurality of tires 11, within short times. Further, the described method provides a non-destructive measuring procedure. Additionally, the apparatus according to the present invention is capable of analyzing different sizes of tires 11.

LIST OF REFERENCE SIGNS 10 apparatus
11 tire
12 magazine
13 lateral rolls
14 transport rolls
15 pivoted retainers
16 rail
17 carriage
18 NMR measuring system
18a NMR sensor
19 camera
20 coil
21 permanent magnet
24 traverse actuator
25 vertical actuator
26 control unit
27 computer
28 magnetic field lines of permanent magnet
29 field lines of coil
$P_n$ measuring points
$T_{2c}$ relaxation times
A-G positions on a tire

The invention claimed is:

1. A method for analyzing at least one material characteristic of an elastomeric material in a tire under evaluation using a nuclear magnetic resonance measuring system comprising a nuclear magnetic resonance sensor, the method comprising:
   a) automatically detecting a location of a tread block of the tire by carrying out a first nuclear magnetic resonance measuring cycle comprising the following steps:
      aa) positioning a nuclear magnetic resonance sensor at a first measuring point located away from the external surface of the tire;
      ab) applying a first exciting signal to the tire by said nuclear magnetic resonance sensor at the first measuring point;
      ac) receiving a first feedback signal resulting from said first exciting signal;
      ad) storing the first feedback signal and the position of the first measuring point;
      ae) positioning said nuclear magnetic resonance sensor at another measuring point located away from the external surface of the tire;
      af) again applying the first exciting signal to the tire by said nuclear magnetic resonance sensor at the another measuring point;
      ag) receiving another feedback signal resulting from said again applied first exciting signal;
      ah) storing the another feedback signal and the position of the another measuring point;
      ai) detecting the location of the tread block by analyzing the intensities of the feedback signals received in ac) and ag); and
   b) carrying out a second nuclear magnetic resonance measuring cycle at the location of said tread block comprising;
      ba) positioning said nuclear magnetic resonance sensor at the tread block in direct contact with an external surface of said tread block;
      bb) applying a second exciting signal to said tread block by said nuclear magnetic resonance sensor;
      bc) receiving a second feedback signal resulting from the said second exciting signal;
      bd) storing the second feedback signal and the position of the tread block;
      be) comparing the second feedback signal with at least one conventionally known a priori reference signal in order to determine the at least one material characteristic of the elastomeric material; and
      bf) providing the determined material characteristic to a user in order to facilitate evaluation of the tire.

2. The method according to claim 1, wherein, in said first nuclear magnetic resonance measuring cycle, said first exciting signal is formed by a single pulse or a small amount of pulses.

3. The method according to claim 1, wherein, in said second nuclear magnetic resonance measuring cycle, said second exciting signal is formed by a plurality of pulses.

4. The method according to claim 1, wherein, after conducting said second nuclear magnetic resonance measuring cycle, said nuclear magnetic resonance sensor is moved in at least one direction with respect to the surface of the tire.

5. The method according to claim 1, wherein, in conducting said first nuclear magnetic resonance measuring cycle, the nuclear magnetic resonance sensor is positioned about 1 to 3 mm from the surface of the tire.

6. The method according to claim 1, wherein, after conducting said second nuclear magnetic resonance measuring cycle, the nuclear magnetic resonance sensor is moved from the surface of the tire in order to rotate the tire to the next measuring point.

7. The method according to claim 1, wherein, after having measured a predetermined number of measuring points of the tire, said nuclear magnetic resonance sensor is moved in a horizontal direction to another tire.

8. An apparatus configured for carrying out the method according to claim 1, comprising:
a magazine configured for holding and positioning at least one tire;
a nuclear magnetic resonance measuring system comprising a nuclear magnetic resonance sensor;
a positioning means for moving said nuclear magnetic resonance sensor in at least one direction with respect to the tire when the tire is positioned in the magazine;
a driving means for driving the tire with respect to its rotational axis;
a control unit configured for controlling the positioning means and the driving means; and
a computer connected with the control unit and the nuclear magnetic resonance measuring system.

9. The apparatus according to claim 8, wherein said computer comprises storing means for storing a nuclear magnetic resonance measuring program and/or a nuclear magnetic resonance sensor control program.

10. The apparatus according to claim 8, wherein said first exciting signal is formed as a single pulse or a small amount of pulses.

11. The apparatus according to claim 8, wherein said second exciting signal comprises a plurality of pulses.

12. The apparatus according to claim 8, wherein said positioning means for moving the nuclear magnetic resonance sensor comprises a driven carriage guided in a horizontal direction on a rail.

13. The apparatus according to claim 8, wherein said positioning means for moving the nuclear magnetic resonance sensor comprises a vertical actuator configured for positioning the nuclear magnetic resonance sensor in a vertical direction and/or a transverse actuator configured for adjusting the position of the nuclear magnetic resonance sensor in a transverse direction.

14. The apparatus according to claim 8, wherein said magazine holds a plurality of tires.

15. The apparatus according to claim 8, wherein a camera or another sensor is provided in order to monitor the position of the nuclear magnetic resonance sensor.

16. The apparatus according to claim 8, wherein said driving means comprises at least one driven transport roll co-operating with the surface of the tire under evaluation.

17. The apparatus according to claim 8, comprising lateral rolls configured for fixing the tire under evaluation in its lateral position and/or a pivoted retainer.

18. The apparatus according to claim 8, wherein said control means drives the driving means to predetermined measuring points of the tire under evaluation.

\* \* \* \* \*

UNITED STATES PATENT AND TRADEMARK OFFICE
CERTIFICATE OF CORRECTION

| | | |
|---|---|---|
| PATENT NO. | : 8,154,283 B2 | Page 1 of 1 |
| APPLICATION NO. | : 12/086863 | |
| DATED | : April 10, 2012 | |
| INVENTOR(S) | : Oliver Albohr et al. | |

It is certified that error appears in the above-identified patent and that said Letters Patent is hereby corrected as shown below:

Claim 1, col. 8, line 55, delete "the" before --said second--.

Signed and Sealed this
Tenth Day of July, 2012

David J. Kappos
*Director of the United States Patent and Trademark Office*